(12) United States Patent
Denyer et al.

(10) Patent No.: US 9,744,319 B2
(45) Date of Patent: Aug. 29, 2017

(54) DRUG DELIVERY APPARATUS AND METHOD

(75) Inventors: Jonathan Stanley Harold Denyer, Chichester (GB); Anthony Dyche, Hayling Island (GB); Michael James Robbert Leppard, Hunston (GB); Ian Thomas Petherbridge, Bognor Regis (GB); Alphonsus Tarcisius Jozef Maria Schipper, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 903 days.

(21) Appl. No.: 13/508,052

(22) PCT Filed: Nov. 2, 2010

(86) PCT No.: PCT/IB2010/054951
§ 371 (c)(1),
(2), (4) Date: Jul. 13, 2012

(87) PCT Pub. No.: WO2011/058477
PCT Pub. Date: May 19, 2011

(65) Prior Publication Data
US 2012/0266870 A1    Oct. 25, 2012

(30) Foreign Application Priority Data
Nov. 11, 2009    (EP) .................................... 09175628

(51) Int. Cl.
*A61M 15/00*    (2006.01)
*A61M 11/00*    (2006.01)

(52) U.S. Cl.
CPC ....... *A61M 15/0085* (2013.01); *A61M 11/005* (2013.01); *A61M 2205/6054* (2013.01)

(58) Field of Classification Search
CPC .. A61M 11/00; A61M 11/005; A61M 11/006; A61M 11/007; A61M 11/06;
(Continued)

(56) References Cited

U.S. PATENT DOCUMENTS 5,170,782 A      12/1992  Kocinski
5,593,390 A  *   1/1997   Castellano et al. ........... 604/187
(Continued)

FOREIGN PATENT DOCUMENTS

EP    1257913 A2    11/2002
EP    1800705       6/2007
(Continued)

*Primary Examiner* — Justine Yu
*Assistant Examiner* — Timothy Stanis
(74) *Attorney, Agent, or Firm* — Michael W. Haas (57) ABSTRACT

A nebulizer (1) comprises one or more removable components (5,7,9,13), for example a mesh assembly (9), mouthpiece, plunger assembly (7) and medication chamber (13), each having an associated data carrier (5a, 7a, 9a). The data carrier (5a, 7a, 9a) can be used to store information indicating the type of removable component (5,7,9,13) that is fitted to the nebulizer (1). A removable component (5,7,9,13) may be from a set of such removable components. For example, a mouthpiece (5) fitted to the nebulizer (1) may be from a set of mouthpieces having different flow rates. The data carrier (5a, 7a, 9a) may also be used to control operation of the nebulizer (1). A data carrier (9a) attached to a mesh (9) may be used to prevent the nebulizer (1) from being used when the mesh (9) has been used a predetermined number of times.

18 Claims, 7 Drawing Sheets

(58) Field of Classification Search
CPC .. A61M 11/08; A61M 15/00; A61M 15/0021; A61M 15/008; A61M 15/0085; A61M 2205/27; A61M 2205/273; A61M 2205/276; A61M 2205/60; A61M 2205/6018; A61M 2205/6063; A61M 2205/6072; A61M 2205/6081; A61M 2205/6054
USPC ............ 128/202.22, 202.27, 203.12, 203.14, 128/203.15, 203.16, 203.23, 203.24, 128/200.14, 200.16
See application file for complete search history.

(56) References Cited

U.S. PATENT DOCUMENTS

| | | | |
|---|---|---|---|
| 5,938,117 | A | 8/1999 | Ivri |
| 6,405,934 | B1 | 6/2002 | Hess et al. |
| 6,651,650 | B1 | 11/2003 | Yamamoto et al. |
| 6,851,626 | B2 * | 2/2005 | Patel et al. ............... 239/338 |
| 6,983,747 | B2 | 1/2006 | Gallem et al. |
| 2002/0157662 | A1 * | 10/2002 | Stenzler ............ A61M 15/0065 128/200.16 |
| 2003/0146300 | A1 | 8/2003 | Denyer et al. |
| 2004/0094152 | A1 | 5/2004 | Harvey et al. |
| 2004/0158349 | A1 | 8/2004 | Bonney et al. |
| 2004/0231667 | A1 | 11/2004 | Horton et al. |
| 2005/0081846 | A1 * | 4/2005 | Barney ................. 128/200.23 |
| 2006/0243277 | A1 | 11/2006 | Denyer |
| 2007/0074722 | A1 | 4/2007 | Giroux et al. |
| 2007/0076067 | A1 | 4/2007 | Hamano et al. |
| 2007/0163583 | A1 | 7/2007 | Brand et al. |
| 2008/0060641 | A1 | 3/2008 | Smith et al. |
| 2009/0120431 | A1 * | 5/2009 | Borgschulte et al. ... 128/200.23 |
| 2009/0126731 | A1 * | 5/2009 | Dunsmore ........ A61M 16/0096 128/203.12 |
| 2009/0133691 | A1 | 5/2009 | Yamada et al. |
| 2009/0194104 | A1 * | 8/2009 | Van Sickle .............. 128/203.12 |
| 2009/0200397 | A1 | 8/2009 | Sheiman |
| 2011/0120456 | A1 * | 5/2011 | Immel ............... A61M 15/0085 128/200.23 |
| 2012/0285446 | A1 * | 11/2012 | Van Der Mark ........ 128/200.14 |

FOREIGN PATENT DOCUMENTS

| | | |
|---|---|---|
| JP | H5277188 A | 10/1993 |
| JP | 8317978 A | 12/1996 |
| JP | 2002540857 | 12/2002 |
| JP | 2004503338 | 2/2004 |
| JP | 2005509499 A | 4/2005 |
| JP | 2006506150 A | 2/2006 |
| WO | WO0158236 A2 | 8/2001 |
| WO | WO03043684 A1 | 5/2003 |
| WO | WO 2006084543 A1 * | 8/2006 |

* cited by examiner

SECTION X - X

DRUG DELIVERY APPARATUS AND METHOD

FIELD OF THE INVENTION

The invention relates to a drug delivery apparatus and method and in particular to a nebulizer used for drug delivery, and a method of operating such a nebulizer.

BACKGROUND OF THE INVENTION

Nebulizers, or atomizers as they are sometimes called, are devices that generate a fine spray or aerosol, usually of liquid. A particularly useful application for nebulizers is to provide a fine spray containing a dissolved or a suspended particulate drug for administration to a patient by inhalation.

Piezo-mesh based nebulizers are commonly used to generate aerosols in such drug delivery apparatus, whereby a piezoelectric element vibrates a FIG. 7 shows a flow chart describing the steps performed by an embodiment of the present invention.

DETAILED DESCRIPTION OF THE EMBODIMENTS

The embodiments below will be described in relation to piezo-mesh type drug delivery apparatus. It is noted, however, that some embodiments are not necessarily limited to such piezo-mesh drug delivery apparatus, for example the embodiments relating to nebulizers having interchangeable components such as mouthpieces and medication chambers. Also, it is noted that the term nebulizer can be used interchangeably with the term drug delivery apparatus or atomizer, and is intended to cover other forms and designs of nebulizer other than the specific type of nebulizer described below and illustrated in the Figures.

Figure 1:
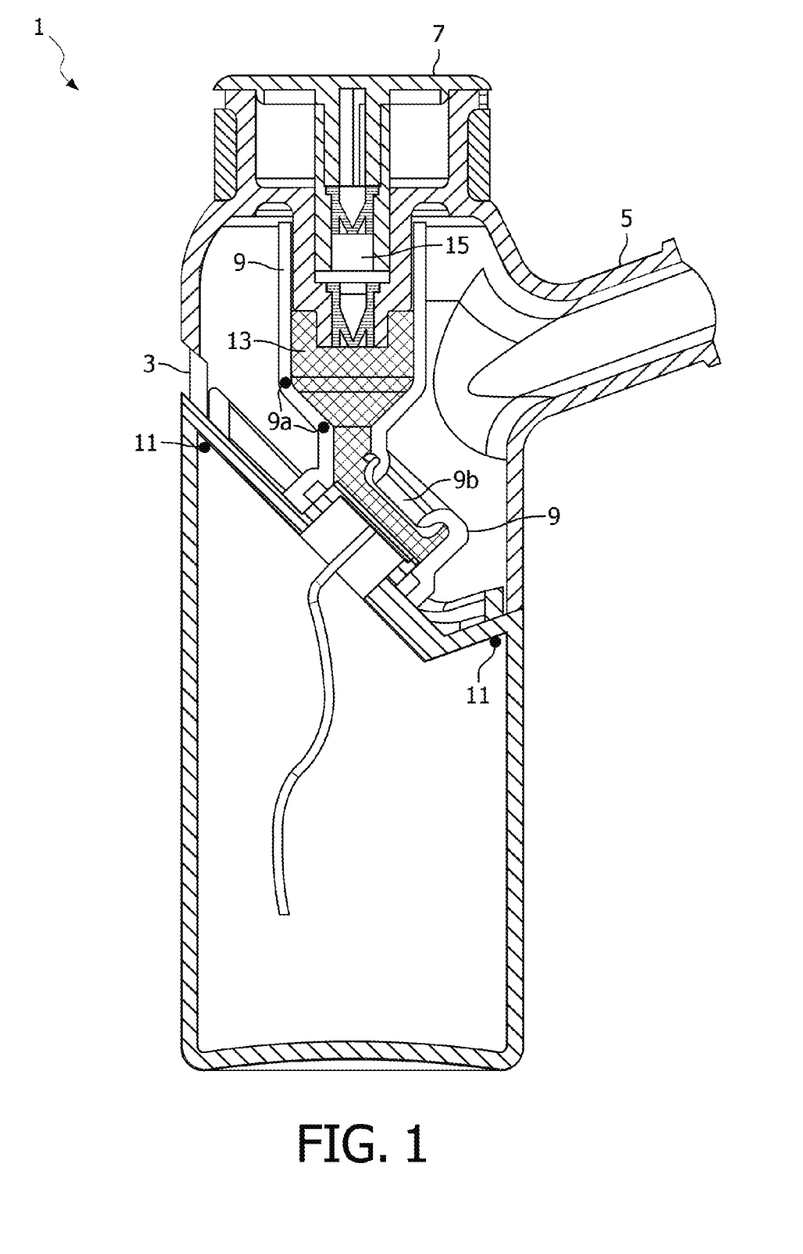

FIG. 1 shows a nebulizer 1 according to an embodiment of the present invention. The nebulizer 1 comprises a body 3 which receives one or more removable components (i.e. interchangeable parts), such as a mouthpiece 5, a plunger assembly 7 and a mesh assembly 9. The mesh assembly 9 comprises a mesh 9b, which is vibrated by a piezoelectric element to generate a fine spray or aerosol. According to one aspect of the invention the mesh assembly 9 also comprises a data carrier 9a. The data carrier 9a communicates with a data reader 11 mounted in the nebulizer 1, for example in the body of the nebulizer. In this particular embodiment the data carrier 9a comprises an RFID tag and the data reader 11 an antenna, each comprising a coil (with FIG. 1 showing a cross section of each coil loop, the coil planes being perpendicular to the plane of the image). The operation of an RFID tag and antenna will be familiar to those skilled in the art. The invention is intended to cover the use of any type of RFID tagging system including, but not limited to, passive RFID tags (i.e. which are powered from the energy received from the associated antenna) or active RFID tags (i.e. which are self-powered). As discussed later in the application, other forms of data carrier and data reader are also envisaged, without departing from the scope of the invention.

The data carrier 9a associated with the mesh 9b provides information relating to the mesh 9b to the nebulizer 1, as will be described later in the application.

In the embodiment of FIG. 1 it can be seen that the body of the mesh assembly 9 also forms a medication chamber 13. As such, the data carrier 9a can also be used to provide information relating to the medication chamber 13 to the nebulizer 1. The plunger assembly 7 comprises a medication metering chamber 15. The medication metering chamber 15 is arranged to feed the drug to be nebulized to the nebulation device for nebulization, while the medication chamber 13 is arranged to hold and retain any of the drug in excess of the volume held in the medication metering chamber 15. This allows a unit dose (i.e. vial) of a drug to be nebulized to be poured into a reservoir, but only the metered volume of the medication metering chamber 15 to be nebulized during treatment, with the remainder or excess of the drug being retained in the medication chamber 13. Further details of the medication metering chamber 15 and its operation can be found in United States patent US2003/0146300A1.

Although the embodiment of FIG. 1 shows the medication chamber 13 being formed using the mesh assembly 9, it is noted that the medication chamber can be formed as a separate physical entity, in which case the medication chamber could have a separate data carrier for providing information relating to the medication chamber to the nebulizer (i.e. a separate data carrier from that associated with the mesh).

Figure 2A:
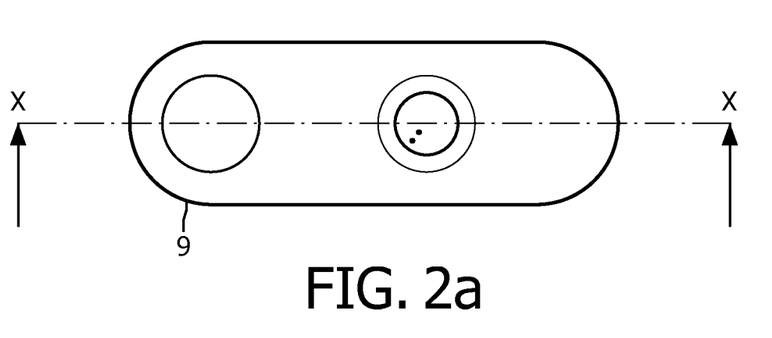
Figure 2B:
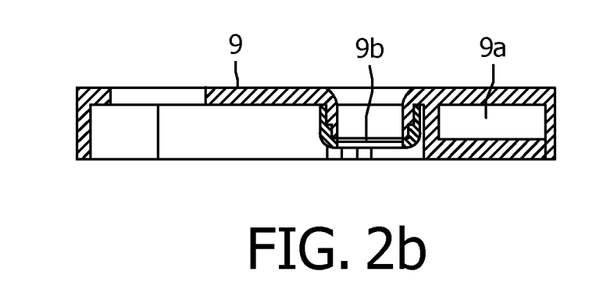
Figure 2C:
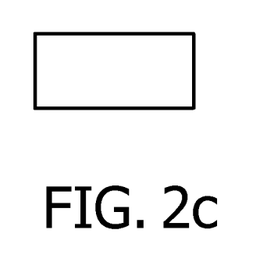

FIGS. 2a to 2c show in greater detail a mesh assembly 9 that is configured differently to the mesh assembly 9 of FIG. 1. FIG. 2a shows a plan view of the mesh assembly 9. FIG. 2b shows a side sectional view through section X-X of FIG. 2a. The mesh assembly 9 of this particular embodiment is configured such that the data carrier 9a and mesh 9b lie in the same plane, i.e. co-planar. This has the advantage of enabling the mesh assembly 9 to be attached to a drug pack. FIG. 2c shows an end view of the mesh assembly 9. It will be appreciated that in this particular embodiment the mesh assembly 9 does not form a medication chamber 13 as shown in FIG. 1, which means that the nebulizer 1 would require a separate medication chamber (and possibly a separate data carrier associated with such a medication chamber).

In a further embodiment, not shown in FIGS. 2a-2c, the mesh assembly 9 may comprise the mesh 9b, the metering chamber and the data carrier 9a. The data carrier may provide information on the mesh and the metered dose to the nebulizer which information may be used by a clinician for example for error checking. For example when the total time of a treatment for a patient is longer then would be expected based on a flow rate of the nebulizer and information from the data carrier on the drug dose and metering chamber volume the clinician may conclude that the mesh needs to be replaced.

Figure 3A:
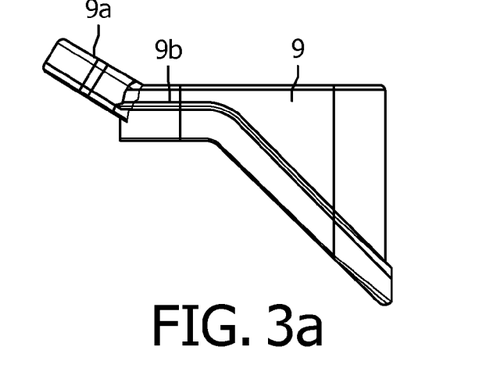
Figure 3B:
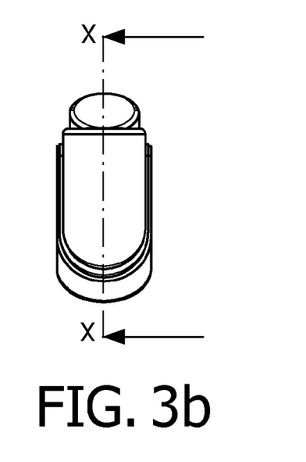
Figure 3C:
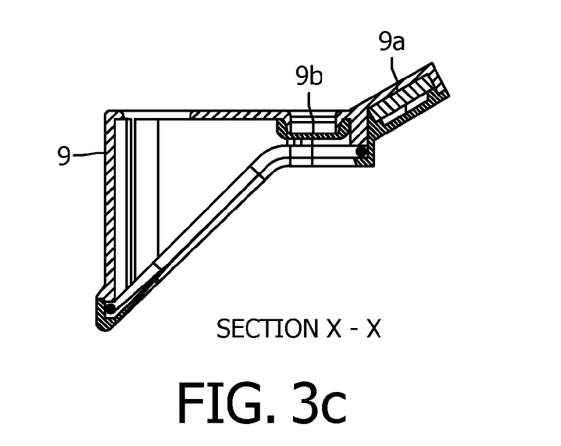

FIGS. 3a to 3c show a further alternative configuration of a mesh assembly 9. FIG. 3a shows a side elevation of the mesh assembly 9, which comprises the data carrier 9a and the mesh 9b. FIG. 3b shows an end elevation, while FIG. 3c shows a sectional view through section X-X of FIG. 3b. According to this particular embodiment the data carrier 9a lies in a different plane to that of the mesh 9b, which may be desirable is certain applications, for example to enable the data carrier 9a to be located more closely to a corresponding data reader 11 of the nebulizer. It will be appreciated that various configurations for mounting the data carrier 9a and mesh 9b are possible, depending on the particular application and the type of nebulizer being used.

The data carrier 9a associated with a mesh 9b of a mesh assembly 9 contains information pertaining to the mesh 9b, which can be read by the data reader 11 of the nebulizer 1. For example, the data carrier 9a may be used to identify the type of mesh 9b being used. The data carrier 9a may contain information on the intended use or lifespan of the mesh 9b, for example how many times the mesh 9b should be used before being replaced. Preferably the whole mesh assembly 9 (including the data carrier 9a and mesh 9b) is replaced after a predetermined number of uses.

Alternatively, if the data carrier 9a and the mesh 9b are detachably connected to the body of the mesh assembly 9, then the data carrier 9a and mesh 9b may be replaced independently of the main body of the mesh assembly 9. For example, the user may purchase a data carrier 9a and a mesh 9b which are replaced as a set, by fitting a new data carrier 9a and a new mesh 9b to the existing body of the mesh assembly 9.

The information received by the data reader 11 may be used by the nebulizer for a number of purposes. According to one embodiment the information received by the data reader 11 can be used to count the number of times a particular mesh 9b has been used, and then prevent the nebulizer from being operated after the mesh 9b has been used a predetermined number of times. The mesh 9b can therefore be prevented from being used in the drug delivery apparatus when its intended lifespan has expired. Alternatively, or in addition, the nebulizer may be configured to provide some form of indication or warning to the user once the intended lifespan has expired, i.e. rather than preventing the nebulizer from being used entirely. This type of indication or warning encourages the user to replace the mesh, but without preventing the nebulizer from being used.

Figure 4:
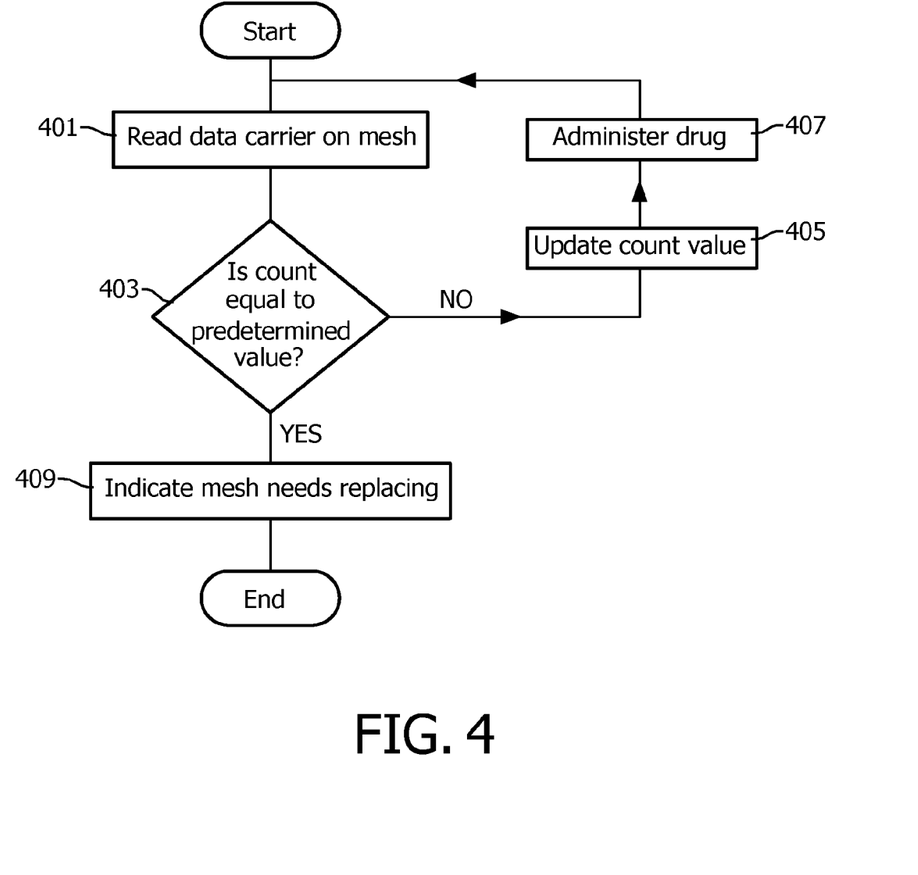

FIG. 4 illustrates the steps that may be performed in a nebulizer having a mesh that has an associated data carrier, as described above in FIGS. 1 to 3. The steps shown in FIG. 4 may be performed as part of a drug delivery operation, for example in response to a user triggering a drug delivery operation. In step 401 the nebulizer reads the data carrier associated with the mesh. In step 403 the nebulizer reads a data field on the data carrier to ascertain a count value relating to the use of the mesh, and determines whether the count value is equal to a predetermined value. For example, if a particular mesh is intended to be used 255 times and is supplied with a count value of 255, which is decremented after each use, step 403 may involve checking whether the count value has reached zero. Alternatively, if the mesh is supplied with a count value of zero which is incremented after each use, step 403 may involve checking whether the count value has reached a predetermined value, i.e. 255 in this particular example.

If it is determined in step 403 that the count value is not equal to a predetermined value, then in step 405 the count value is updated (i.e. incremented or decremented), and the nebulizer operated to deliver a drug, step 407.

If it is determined in step 403 that the count value is equal to a predetermined value, thereby indicating that the mesh has been used a predetermined number of times, the nebulizer indicates in step 409 that the mesh requires replacing. This may involve disabling the nebulizer such that the mesh can no longer be used.

As mentioned above, as an alternative to preventing the nebulizer from being operated after the mesh has been used a predetermined number of times, the nebulizer may be configured instead (or in addition) to provide a warning to the user that the mesh should be replaced. For example, the nebulizer may be configured to provide a visual and/or audible warning when the mesh has reached its expected lifespan.

The nebulizer may also be configured to provide such a warning at a predetermined interval prior to the mesh coming to the end of its life, thereby warning the user to purchase a new mesh.

Preferably the updated count value shown in step 405 is stored on the data carrier 9a associated with the mesh 9b. As such, the data reader 11 acts as a data writer in addition to a data reader. In other words, the data reader 11 (for example an antenna) is adapted to transmit data to the data carrier 9a, as well as reading data from the data carrier 9a. In such an embodiment the data carrier will include, for example, an electrically erasable memory as will be familiar to those skilled in the art, such as an Electrically Erasable Programmable Read Only Memory (EEPROM). Other forms of data carriers that are capable of storing and updating a count value are also intended to be embraced by the present invention.

As an alternative to the above, the updated count value may be stored in the nebulizer itself. With such an embodiment the data carrier 9a may have a simpler form of memory device, such a Read Only Memory (ROM) which is programmed once during manufacture with a count value corresponding to the intended lifespan of the mesh. However, the former method has the advantage of retaining the count value with the device that is actually being monitored, which provides a more secure application.

It is noted that the data carrier 9a and data reader 11 can be realized in alternative ways to using an RFID tag and an antenna. For example, other identifying means such as a barcode, DX or serial interface can be used to communicate information between the mesh and the nebulizer. However, using an RFID tag and an antenna has the advantage of not requiring any interconnecting electrical contacts, which could otherwise become degraded in the type of environment found within a nebulizer device.

In addition to the data carrier 9a being used to store information relating to the use of the corresponding mesh 9b, it is noted that the data carrier 9a may also be used to store other information, such as information relating to the drug being dispensed. In other words, since the data carrier 9a is used to store information about the use of the nebulizer, the data carrier 9a may also be used to store other information relating to such use, including the number of drug vials to be dispensed. Thus, if a mesh of the nebulizer is replaced at the same time as the drug container, the data carrier 9a of the mesh can be used to indicate when the drug container needs to be replaced. Also, as indicated above in FIG. 1, if the mesh assembly 9 forms part of the medication chamber, then the data carrier 9a may also store information relating to the medication chamber.

Figure 5:
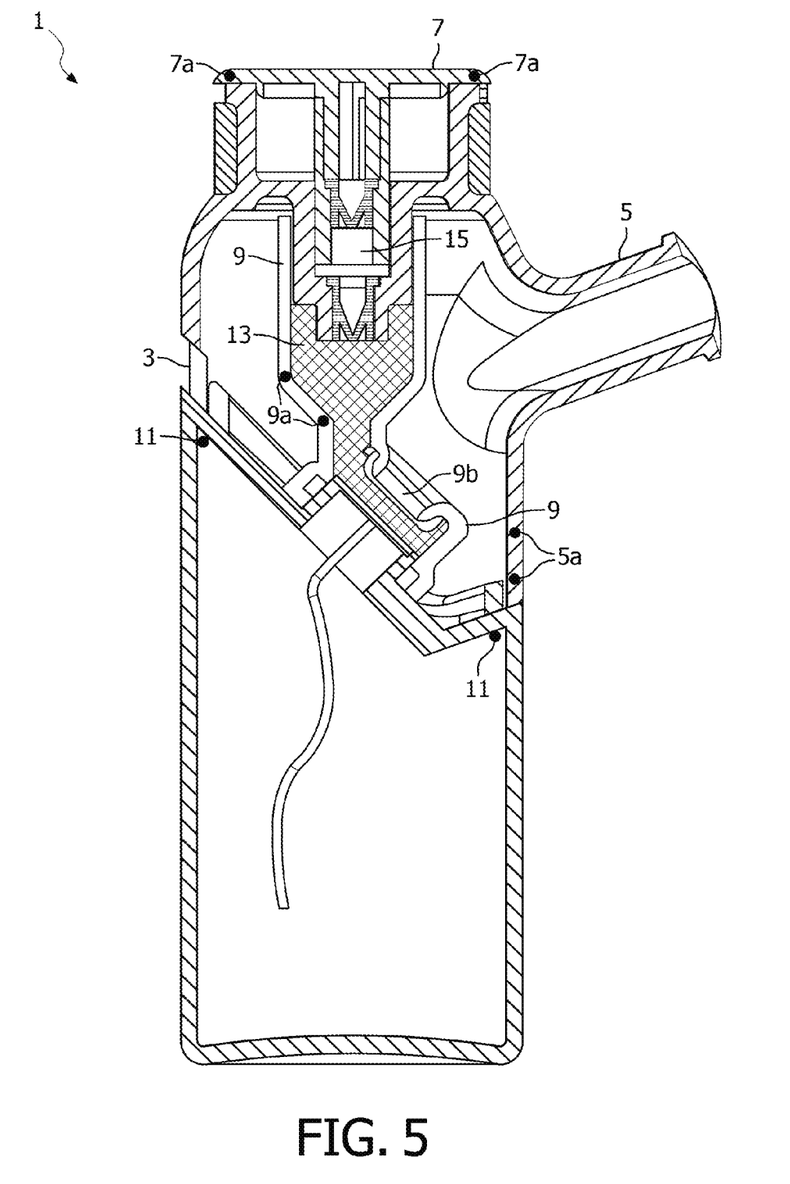

FIG. 5 shows a nebulizer 1 according to another embodiment of the present invention. The nebulizer 1 comprises a body 3 for receiving one or more removable components, such as a mouthpiece 5, a plunger assembly 7 and a mesh assembly 9. As with FIG. 1, the mesh assembly 9 forms a medication chamber 13 (although it is noted that these could be separate physical components, without departing from the scope of the invention). The plunger assembly 7 comprises a medication metering chamber 15. According to this embodiment the mesh assembly 9 comprises a first data carrier 9a, the mouthpiece 5 comprises a second data carrier 5a, and the plunger assembly 7 comprises a third data carrier 7a. The first data carrier 9a associated with the mesh assembly 9 also doubles as a medication chamber data carrier for this particular embodiment. Each of the data carriers 5a, 7a and 9a communicate with a data reader 11 mounted in the body 3 of the nebulizer 1.

One or more of the removable components 5, 7 or 9 may be a removable component associated with a set of such removable components (i.e. a form of interchangeable part selected from a set of such interchangeable parts). For example, the removable mouthpiece 5 can be from a set of different mouthpieces that may be fitted to the nebulizer. The nebulizer comprises control means for controlling the operation of the nebulizer depending on the particular removable component that is attached to the nebulizer at a given time.

Figure 6:
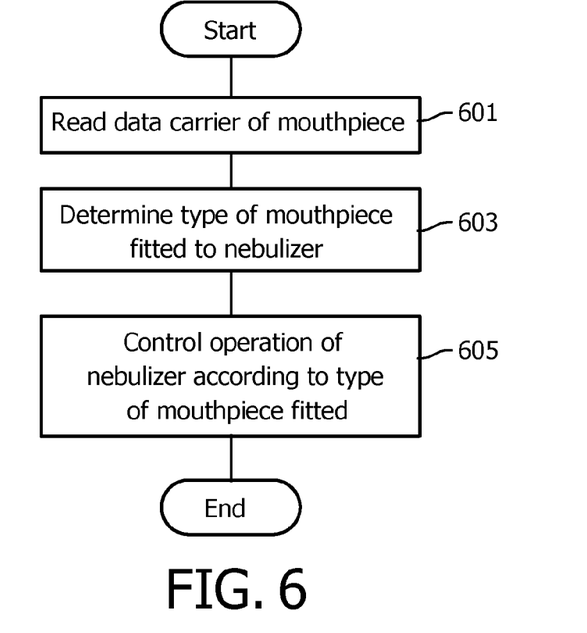
Figure 7:
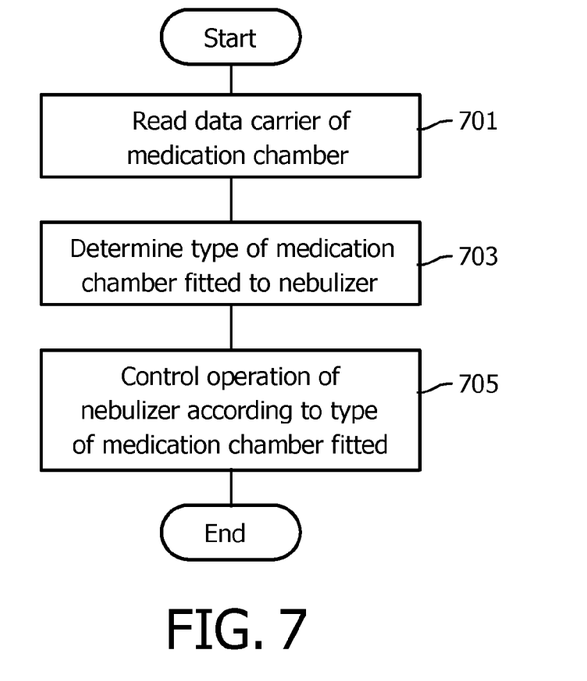
Figure 8:
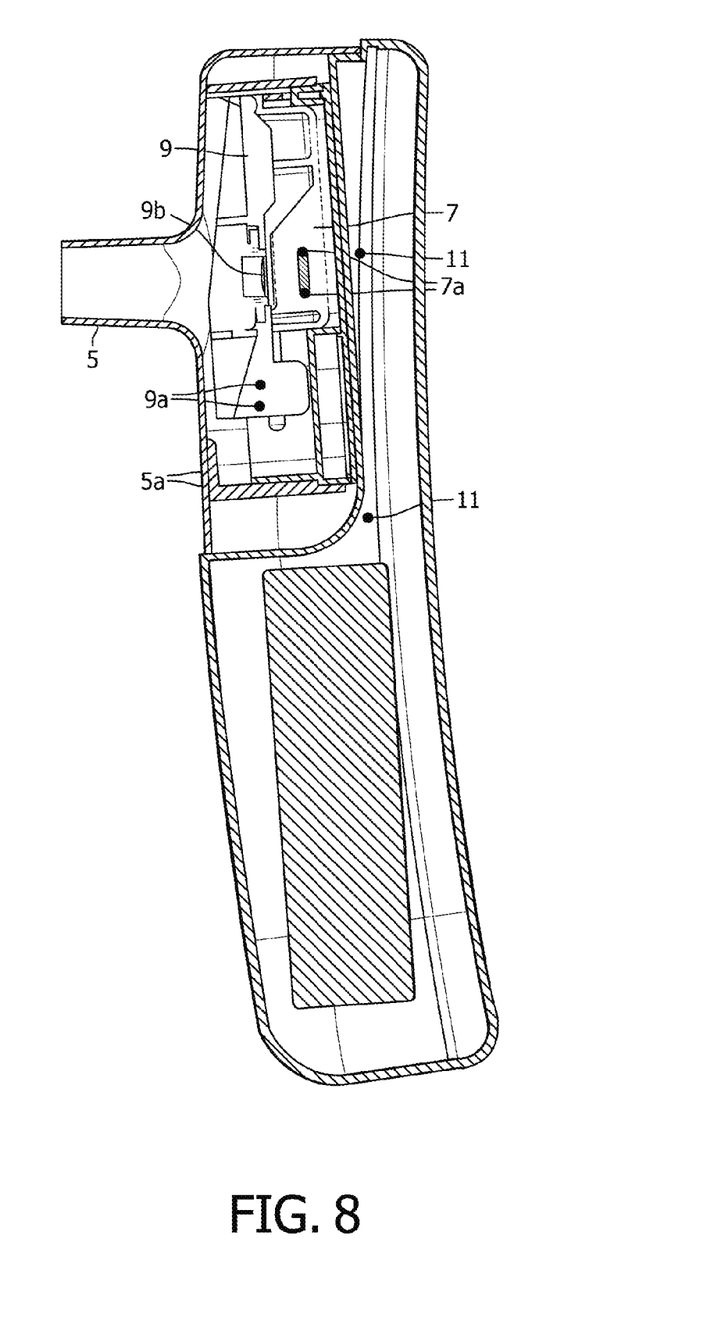
FIG. 8 shows a nebulizer according to another embodiment of the present invention.

For example, FIG. 6 illustrates the steps that may be performed in a nebulizer depending on the type of mouthpiece fitted to the nebulizer. In step 601 the nebulizer reads the data carrier 5a of the mouthpiece 5. In step 603 the nebulizer determines the type of mouthpiece 5 that is fitted to the nebulizer using the information gathered from the data carrier 5a. Then, in step 605, the nebulizer adjusts or controls the operation of the nebulizer according to which type of mouthpiece 5 is fitted to the nebulizer.

The mouthpiece 5 is part of a set of associated mouthpieces that may be used with the nebulizer, for example depending on the particular preference of the user, or which is best suited for delivery of a particular type of drug.

For example, patients could be supplied with two or more mouthpieces with varying resistances to suit their personal preference, such as a first mouthpiece giving a high resistance of about 14-18 liters/min, a second mouthpiece giving a low resistance of about 24-36 liters/min, and a third mouthpiece giving a resistance of about 40-60 liters/min. The control software in the nebulizer needs to know which mouthpiece is fitted in order to enable the nebulizer to operate correctly, and the data carrier 5*a* mounted on the mouthpiece can be used to store such information during manufacture.

FIG. 7 illustrates the steps that may be performed in a nebulizer depending on the type of medication chamber 13 fitted to the nebulizer. In step 701 the nebulizer reads the data carrier of the medication chamber 13 (which would be the data carrier 9*a* in FIGS. 1 and 5 due to the medication chamber 13 being formed from the mesh assembly 9—a separate data carrier being provided when the medication chamber is formed from a separate physical entity to that of the mesh assembly). In step 703 the nebulizer determines the type of medication chamber that is fitted to the nebulizer using the information gathered from the data carrier 9*a*. Then, in step 705, the nebulizer adjusts or controls the operation of the nebulizer according to which type of medication chamber is fitted to the nebulizer.

The medication chamber 13 is part of a set of associated medication chambers 13 that may be used with the nebulizer, for example depending on which particular medication chamber is best suited for delivery of a particular type of drug.

In some applications more than one volume of drug can be delivered from the same drug pack by using different medication chambers. In such applications the drug dose information on the data carrier 9*a* associated with the mesh 9*b* may not be sufficient for the nebulizer software to accurately determine the drug dose. This is improved by adding a data carrier to the medication chamber 13 as described above (or to the metering system) for the medication chamber 13 to uniquely identify the drug dose which has been placed in the device.

The nebulizer may be configured to perform other features based on the information detected by the data reader 11. For example, the nebulizer can be configured to only start a treatment once a predetermined set of components are detected as being attached to the nebulizer, such as when the mesh assembly 9, mouthpiece 5, plunger assembly 7 and medication chamber 13 have been detected as being present.

Although the embodiment of FIG. 5 shows a single data reader 11 being provided for communicating with each of the data carriers 5*a*, 7*a* and 9*a* relating to the mouthpiece 5, plunger assembly 7 and mesh assembly 9 respectively, it is noted that the nebulizer may comprise one or more data readers 11 for communicating with one or more data carriers. As with the embodiment of FIG. 1, the data carriers 5*a*, 7*a* and 9*a* may be RFID tags and the data reader(s) 11 an antenna, although other forms of communication means are also intended to be embraced by the present invention.

The range of the RFID system may be set so that only assembled components and their associated data carriers are detected by the data reader(s) 11. This has the advantage that RFID tagged components located nearby, but not affixed to the nebulizer, are not detected by the data reader(s) 11.

This may be achieved by designing and positioning the data reader 11 and associated data carriers 5*a*, 7*a*, 9*a* so that the field of operation is limited to the shortest range required, and positioning the data carriers close to the data reader.

FIG. 8 shows an alternative embodiment, whereby the configuration of the nebulizer is adapted to enable the data carrier 7*a* associated with the plunger assembly 7 to be brought into closer proximity with the data reader 11, thereby enabling the range of the RFID system to be reduced, and hence reducing the possibility of interference from other devices. As with FIG. 5, the nebulizer comprises a mouthpiece 5 having an associated data carrier 5*a*, a plunger assembly 7 having an associated data carrier 7*a*, and a mesh assembly 9 having an associated data carrier 9*a*.

The nebulizer described in the embodiments above may also adopt one or more other strategies to help reduce or prevent detection of unwanted items by the radio frequency tagging system. For example, shielding may be provided on the side of the data reader 11 that is opposite to the side where the data carriers 5*a*, 7*a* and 9*a* are positioned.

In the embodiments described above the RFID data transmission could be interrupted by an external RF source such as the piezoelectric element used to vibrate the mesh, or by mobile phones that are within close proximity. However, the former does not have a degrading effect on the operation of the RFID system, since the RFID tags are normally read prior to the drug delivery operation itself, i.e. prior to the piezoelectric circuit being activated, and hence prior to such interference being present. Interference from other sources such as mobile phones can be overcome using data correction techniques commonly found in wireless technology, as will be familiar to a person skilled in the art.

The RFID system may consist of an integrated circuit with a copper coil, which can be encapsulated within a thin plastic film. This may typically comprise a product that is about 10 mm in diameter and about 1-2 mm tick. It will be appreciated, however, that other dimensions can also be used depending on the particular nebulizer, and without departing from the scope of the invention.

The RFID tag may be integrated into a plastic housing either mechanically, by potting or over molding to produce a hermetically sealed assembly as shown in FIGS. 2*a* to 2*c* or 3*a* to 3*c*. This plastic housing can also incorporate the mesh required for aerosol generation which is typically 10 mm diameter and 0.025-0.5 mm thick, this can also be mounted mechanically or over molded. This generates an assembly typically 35×20 mm and 2-3 mm thick or if the components are mounted co axially 25 mm diameter and 2-3 mm thick. It will be appreciated, however, that other mounting arrangements and configurations may be used without departing from the scope of the invention.

It is noted that data carriers may also be added to other removable components of the nebulizer, such as ID cards or labels.

Table 1 below illustrates some parameters of the reader coil and tag coils that may be used, for example, in a nebulizer according to an embodiment of the invention.

TABLE 1

| | Diameter [cm] | Windings | Distance [cm] | Offset [cm] | Alpha |
|---|---|---|---|---|---|
| Reader coil | 4.0 | 2 | 0.0 | | 0 |
| Mesh coil | 1.0 | 18 | 1.3 | 1.4 | 0 |
| Mouthpiece coil | 1.0 | 18 | 1.5 | 1.5 | 45 |
| Plunger | 1.0 | 18 | 5.6 | 3.0 | 45 |
| ID card coil | | | 2.0 | 0.0 | 0 |
| Label coil | | | 2.0 | 0.0 | 0 |

Diameter: Diameter of coil
Windings: Number of windings
Offset: Offset from center of reader coil
Alpha: Angle from plane parallel to reader coil plan The antenna may be a dedicated antenna, which can be tuned to 13.56 MHz, for example. The antenna may comprise four circular windings with a diameter of 40 mm.

It is also noted that the RFID tag associated with the mesh may contain a number of fields related to the mesh and/or the drug and/or the delivery system. For example, a "Vial Count Remaining" field may be used to determine when the tag can no longer be used as it is decremented by one each time a treatment is delivered.

Although the embodiments described above have been made in relation to interchangeable mouthpieces, medication chambers or meshes, it will be appreciated that the invention is equally applicable to any other interchangeable part of a drug delivery apparatus, and in particular interchangeable parts from a set of such interchangeable parts.

The term "removable component" is intended to embrace a part or component of the nebulizer, at least part of which contributes to the actual functioning of the nebulizer, rather than a non-functioning part such as the actual drug to be dispensed. In other words, at least part of the removable component is a physical part of the actual nebulizer, which contributes to the physical working of the nebulizer.

Furthermore, although the embodiments of FIGS. 1 and 5 show a nebulizer having a removable mesh assembly, a removable mouthpiece, a removable plunger assembly and removable medication chamber, it will be appreciated that not all of these components need necessarily be removable, or be from sets of interchangeable parts. For example, in the embodiment of FIG. 1 the mouthpiece and medication chamber may be fixed components, rather than removable components.

It will be appreciated from the above that RFID tags are ideally suited to the described embodiments, as they require no electrical contacts that may be affected by the saline based drugs often used in the drug products to be inhaled, which would otherwise affect alternative embodiments such as DX or serial interfaces that require electrical contacts. RFID tags are also more suitable than bar codes as the vial count can be decremented in the tag itself after each treatment which is more secure than reading a bar code and decrementing the count within the delivery system itself. However, as mentioned above, the invention is not limited to just RFID tags, and that other identification systems can be used without departing from the scope of the invention.

It is also noted that the invention can be used with piezo-mesh type nebulizers in which the piezoelectric element and the mesh are bonded together, or with piezo-mesh type nebulizers in which the piezoelectric element and mesh are formed separately.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single processor or other unit may fulfill the functions of several units recited in the claims. Any reference signs in the claims shall not be construed so as to limit their scope.

The invention claimed is:

1. A nebulizer comprising:
   a first removable component comprising a first data carrier, wherein the first removable component is a mouthpiece and the first data carrier stores information about the mouthpiece;
   a second removable component comprising a second data carrier, wherein the second removable component is a mesh assembly that is attached to a medication chamber such that the second data carrier stores information related to both the mesh assembly and the medication chamber;
   a third removable component comprising a third data carrier, wherein the third removable component is a plunger assembly, the plunger assembly including a medication metering chamber, the third data carrier storing information related to the plunger assembly; and
   at least one data reader for communicating with the first data carrier of the first removable component, the second data carrier of the second removable component, and the third data carrier of the third removable component, wherein the first removable component, the second removable component, and the third removable component are useable as part of the nebulizer at the same time.

2. A nebulizer as claimed in claim 1, wherein the first removable component, the second removable component, and the third removable component are individual ones of sets of associated removable components.

3. A nebulizer as claimed in claim 2, wherein the at least one data reader is adapted to identify a particular removable component from its associated set of removable components using information contained in the first data carrier of the first removable component, the second data carrier of the second removable component, or the third data carrier of the third removable component.

4. A nebulizer as claimed in claim 2,
   wherein the first removable component is a mouthpiece from a set of removable mouthpieces,
   wherein the mouthpieces in the set of removable mouthpieces are differentiated by their resistance;
   wherein the second removable component is a mesh assembly from a set of removable mesh assemblies; and
   wherein the mesh assemblies in the set of removable mesh assemblies are differentiated by a type of medication in corresponding medication chambers.

5. A nebulizer as claimed in claim 1, further comprising one or more processors configured to execute control software for controlling an operation of the nebulizer, wherein the one or more processors are configured to control the operation of the nebulizer based on information provided by the first data carrier, the second data carrier, and the third data carrier.

6. A nebulizer as claimed in claim 4 wherein the one or more processors are configured such that the operation of the nebulizer is only possible once a of the first, second, and third removable components are detected as being attached to the nebulizer.

7. A nebulizer as claimed in claim 1, wherein the first data carrier, second data carrier, the third data carrier, and the at least one data reader comprise a radio frequency identification (RFID) tagging system.

8. A nebulizer as claimed in claim 7, wherein the first data carrier comprises a first RFID tag, the second data carrier comprises a second RFID tag, the third data carrier comprises a third RFID tag, and the at least one data reader comprises an antenna.

9. A nebulizer as claimed in claim 7, wherein the RFID tagging system is configured to communicate with RFID tags mounted in removable components attached to the nebulizer.

10. A nebulizer as claimed in claim 1, wherein, in use, the same single data reader communicates with the first data carrier, the second data carrier, and the third data carrier.

11. A nebulizer as claimed in claim 1, wherein the first data carrier is adapted to store information that indicates a type of mouthpiece formed by the first removable component, and wherein the second data carrier is adapted to store information for preventing a mesh from being used in the nebulizer after a predetermined number of uses.

12. A nebulizer as claimed in claim 1, wherein one or more of the first data carrier or the second data carrier stores a count value, the count value being incremented or decremented after each use of the mesh.

13. A nebulizer as claimed in claim 1, wherein a mesh of the second removable component and the second data carrier are coplanar in the second removable component.

14. A nebulizer, the nebulizer comprising:
a removable mouthpiece comprising an associated first data carrier for communicating, in use, with a data reader provided in the nebulizer, the first data carrier forming part of the mouthpiece such that removal of the mouthpiece removes the first data carrier therewith;
a removable mesh assembly that is attached to a medication chamber such that a second data carrier stores information related to both the mesh assembly and the medication chamber, the removable mesh assembly comprising the second data carrier that communicates, in use, with the data reader; and
a removable plunger assembly comprising a third data carrier, the plunger assembly including a medication metering chamber, the third data carrier storing information related to the plunger assembly.

15. A nebulizer as claimed in claim 14, wherein the removable mouthpiece, the removable mesh assembly, and the removable plunger assembly individually form parts of sets of interchangeable removable components for use with the nebulizer, and wherein the data carriers provide, in use, information relating to which removable components from the sets of interchangeable removable components are being used with the nebulizer.

16. A method of operating a nebulizer, the method being implemented in a computer system including one or more processors configured to execute software, the method comprising:
receiving information from a first data carrier associated with a removable mouthpiece of the nebulizer, the first data carrier storing information about the mouthpiece;
receiving information from a second data carrier associated with a removable mesh assembly of the nebulizer, which is attached to a medication chamber such that the second data carrier stores information related to both the mesh assembly and the medication chamber;
receiving information from a third data carrier associated with a removable plunger assembly, the plunger assembly including a medication metering chamber, the third data carrier storing information related to the plunger assembly;
operating a data reader to receive the information from the first data carrier, the information from the second data carrier, and the information from the third data carrier; and
controlling an operation of the nebulizer based on the information received from the first data carrier, the second data carrier, and the third data carrier.

17. A method as claimed in claim 16, further comprising preventing the nebulizer from being used when the mesh assembly has been used a predetermined number of times.

18. A method as claimed in claim 17, further comprising controlling the operation of the nebulizer based on a type of mouthpiece fitted to the nebulizer, a type of plunger assembly fitted to the nebulizer, a type of medication chamber in the mesh assembly fitted to the nebulizer, and a number of times the mesh of the mesh assembly fitted to the nebulizer has been used.

* * * * *